US005374522A

United States Patent [19]
Murphy et al.

[11] Patent Number: 5,374,522
[45] Date of Patent: Dec. 20, 1994

[54] METHOD FOR RELEASING RNA AND DNA FROM CELLS

[75] Inventors: Kathleen A. Murphy, Spring Valley; Barry D. Epstein; Ira G. Rosen, both of San Diego; Elizabeth D. Dean, El Cajon, all of Calif.

[73] Assignee: Gen-Probe Incorporated, San Diego, Calif.

[21] Appl. No.: 711,114

[22] Filed: Jun. 21, 1991

Related U.S. Application Data

[63] Continuation of Ser. No. 298,765, Jan. 17, 1989, abandoned, which is a continuation of Ser. No. 841,860, Mar. 20, 1986, abandoned.

[51] Int. Cl.$^5$ .................. C12Q 1/68; C07H 21/02; A47J 19/06
[52] U.S. Cl. ........................ 435/6; 536/23.1; 536/25.4; 241/2
[58] Field of Search .............. 435/6; 536/27, 23.1, 536/25.4; 241/2

[56] References Cited

U.S. PATENT DOCUMENTS

| | | | |
|---|---|---|---|
| 2,473,453 | 6/1949 | Shropshire | 260/412.1 |
| 3,172,546 | 3/1965 | Schreiner | 241/23 |
| 3,558,066 | 1/1971 | Alliger | 241/2 |
| 3,983,008 | 9/1976 | Shinozaki et al. | 435/190 |

(List continued on next page.)

FOREIGN PATENT DOCUMENTS

| | | |
|---|---|---|
| 41-10181 | 5/1966 | Japan. |
| 84/02721 | 7/1984 | WIPO. |

OTHER PUBLICATIONS

Matthews et al., *Analytical Biochemistry*, vol. 169 (1988) Jan. 25.
Venner, "Extraction and Testing of Nucleic Acids from Mycobacteria", *Acta biol. med. Germ.*, vol. 11, No. 5/6, 1963, pp. 806–815.
Brown, M. J. et al. "Comparison of Bacterial Extracellular Polymer Extraction Methods", vol. 40, No. a 2, pp. 179–185, Aug. 1980 *Applied and Environmental Microbiology*.

Roberson, B. S. et al. "Studies on Preparation of Bacterial Cell Walls and Criteria of Homogeneity", *Biochemica et Biophysica Acta*, vol. 44, pp. 436–444 (1960).
Lowell, A. M. "Tuberculosis Its Social and Economic Impact and Some Thoughts On Epidemiology", *Mycobacteria A Source Book*, Part B, Kubica G. P. and Wayne, L. E. (Eds) pp. 1021–1032.
Wayne, L. G. et al. "Autolysis and Secondary Growth of *Mycobacterium Tuberculosis* in Submerged Culture" *J. Bacteriol.*, Fol. 93 No. 4 pp. 1374–1381 (1967).
"Future Research in tuberculosis: Prospects and Priorities For Elimination" Report of a Conference Held Jun. 5–7, 1985, Pittsfield, Mass.
Schnaitman, C. A. "Cell Fracitionation" *Manual of Methods For General Bacteriology* Gerhardt et al. (Eds) pp. 52–61 (1981).
Coakley, W. T. et al. "Disruption of Microorganisms" *Advanced Microbial Physiology*, vol. 16, pp. 279–341 (1977).
Hughes, D. E. et al. "The Disintegration of Microorganisms" *Methods in Microbiology*, vol. 5B, pp. 1–54 (1971).
Wayne, L. G. et al. "Isolation of Deoxyribonucleic Acid From Mycobacteria" *J. Bacteriol.* vol. 95, No. 4, pp. 1481–1482 (1968).

(List continued on next page.)

*Primary Examiner*—Mindy B. Fleisher
*Attorney, Agent, or Firm*—Lyon & Lyon

[57] ABSTRACT

A method is disclosed for disrupting cells, including microorganisms, and facilitating thereby the release of cellular components including RNA and DNA into solution. Solutions or suspensions of cells are placed in a container with minute beads of various composition. The container is then placed in an ultrasound bath or otherwise subjected to sonication until the cells disrupt releasing their cellular components, including RNA and DNA. The released RNA and DNA are then available for hybridization with genetic probes.

28 Claims, No Drawings

U.S. PATENT DOCUMENTS

| | | | |
|---|---|---|---|
| 4,038,143 | 7/1977 | Joni | 435/259 X |
| 4,295,613 | 10/1981 | Moore et al. | 241/2 |
| 4,476,225 | 10/1984 | Grigorian et al. | 435/287 |

OTHER PUBLICATIONS

Seiter, J. A. et al. "Application of Polyacrylamide Gel Electrophoresis To The Characterization and Identification of Arthrobacter Species" *Int. J. Syst. Bacteriol*, vol. 30, pp. 460–465 (1980).

Salter, D. N. et al. "Protein utilization In the Young Steer: Digestion and Nitrogen Retention of $^{15}$N-Labelled Rumen Bacterial Protein" *British Journal of Nutrition*, vol. 51, pp. 531–539 (1984).

Closs, O. et al. "The Antigens of *Mycobacterium Bovis*, Strain BCG, Studied by Crossed Immunoelectrophoresis: A Reference system" *Scand. J. Immunol.* vol. 12, pp. 249–263 (1980).

Alliger, H. "Ultrasonic Disruption", American Laboratory, (1975).

Kohne, D. E. et al. "Hydroxyapatite Techniques For Nucleic Acid Reassociation" *Procedures in Nucleic Acid Research*, vol. 2, pp. 500–512.

Salton, M. R. J. "Isolation of Cell Walls From Gram–Positive Bacteria", Methods in Enzymology vol. XXXI Biomembranes Part A, Fleisher S. and Packer L. Eds pp. 653–667.

METHOD FOR RELEASING RNA AND DNA FROM CELLS

This is a continuation of application Ser. No. 07/298,765, filed Jan. 17, 1989, abandoned, which is a continuation of application No. 06/841,860, filed Mar. 20, 1986, abandoned. This application is related to Kohne, D. E., U.S. patent application Ser. No. 456,729, entitled "METHOD FOR DETECTION, IDENTIFICATION AND QUANTITATION OF NON-VIRAL ORGANISMS," filed Jan. 10, 1983, Kohne, D. E., abandoned in favor of U.S. patent application No. 040,737, which issued as U.S. Pat. No. 4,851,330 on Jul. 25, 1989; and U.S. patent application Ser. No. 655,365, entitled "METHOD FOR DETECTING, IDENTIFYING AND QUANTITATING ORGANISMS AND VIRUSES," filed Sep. 4, 1984, Kohne, D. E., abandoned in favor of 353,208, abandoned in favor of 464,717, abandoned in favor of 584,432, abandoned in favor of 07/857,081 which is pending; and U.S. patent application Ser. No. 627,795, entitled "ACCELERATED NUCLEIC ACID REASSOCIATION METHOD," filed Jul. 5, 1984, abandoned; and Kohne, D. E. et al., U.S. patent application No. 816,711 entitled "ACCELERATED NUCLEIC ACID REASSOCIATION METHOD" filed Jan. 7, 1986, (a continuation-in-part of Ser. No. 627,795) abandoned in favor of 587,063, abandoned in favor of 644,879 which issued under U.S. Pat. No. 5,132,207 on Jul. 21, 1992. Al of these disclosures are incorporated by reference herein.

FIELD OF THE INVENTION

The present invention is directed to a method for disrupting cells thereby allowing the cellular constituents to be released into solution. More particularly, the present invention is directed to a method for releasing RNA and DNA from microorganisms wherein a solution of microorganisms is placed in a container which includes small beads of various composition. The container is then placed in an ultrasonic bath until the cells are disrupted and the cellular constituents are released. A variety of additives such as salts, buffers, detergents, genetic probes, antibodies, enzymes, chelators, salts, organic compounds, etc., can also be present in the solution. As a result of the method according to the present invention, an otherwise refractory intact microorganism such as, e.g., *Mycobacterium tuberculosis*, present in a clinical or biological sample in either an open or closed container can be broken open and the cellular constituents contained therein, including RNA and DNA, can be released and made available for in-sample detection, identification, quantitation or other diagnostic procedures utilizing genetic probe or antibody detection technology.

DESCRIPTION OF THE PRIOR ART

The biotechnology revolution has produced great interest in the genetic constituency of cells. As a result, the past 25 years has seen a great degree of effort expended to determine ways to facilitate release of RNA and DNA from within microorganisms. The RNA and DNA contained within a microorganism can, for example, provide valuable information useful in identifying whether an organism is present in a clinical or biological sample. Hybridization reactions involving genetic probes rely on the release of the genetic information from within the cell in order to facilitate hybridization with the complementary sequences of nucleic acids on the genetic probes. Such hybridization reactions can be used to isolate, detect, identify and/or quantify microorganisms which are present in biological samples.

However, while some types of cells are more amenable to disruption and release of their cellular components, other types of cells are more refractory. One such cell, *Mycobacterium tuberculosis*, which is the etiologic agent of tuberculosis, is notoriously difficult to break open. Consequently, it has been much more difficult to expediently and efficiently obtain the RNA or DNA present within these types of refractory organisms in a manner which prevents their identification by probe technology.

Of all the infectious diseases that have plagued man, tuberculosis has probably been responsible for the greatest morbidity and mortality. Even today, when the incidence of tuberculosis in the Western Nations has markedly decreased, tuberculosis still remains one of the world's most prevalent infectious diseases. It is currently estimated that more than half of the world's population is infected with tubercle bacilli. (Youmans, G. P., *Tuberculosis,* W. B. Saunders Company (1979)) The total annual cost of tuberculosis control activities is estimated at about $600 million a year in the United States alone. (Report of a conference, "Future Research in Tuberculosis: Prospects and Priorities for Elimination" 9 (Jun. 5–7, 1985), submitted for publication as a supplement in the *American Review of Respiratory Disease,* (hereinafter, "Pittsfield Report").)

On Jun. 5–7, 1985, the Center for Disease Control (CDC), the National Institutes of Health (NIH), the American Thoracic Society (ATS) and the Pittsfield Antituberculosis Association (PATA) co-sponsored a conference, the objective of which was to identify priority areas for research which might lead to an accelerated decline in tuberculosis morbidity and, ultimately, the elimination of tuberculosis from the United States and the world. Among those obstacles identified as significant to the control and elimination of the disease were the currently available lengthy diagnostic measures.

With approximately 50% of the world's population infected with tubercle bacilli, the World Health Organization (WHO) estimates that at the present time, within one year, as many as 4 to 5 million new infectious cases of tuberculosis will develop. Perhaps an equal number, another 4 to 5 million, of non-infectious cases of tuberculosis will develop in a year's time. In addition to these 8 to 10 million new cases, there are perhaps as many as 3 to 4 million deaths from tuberculosis worldwide per year. ("Pittsfield Report" at p. 14)

The ways in which tuberculosis is defined and identified reflect the state of tuberculosis control technology. As described in the "Pittsfield Report", at p. 17, "[t]uberculosis is still being fought with 19th Century tools-tools which were considered modern at the turn of this century, but which are becoming obsolete as the turn of the next century approaches." Infected persons are defined by their response to the tuberculin test which is basically the same procedure developed by Robert Koch. The procedure remains one of injecting a fairly crude antigen into the skin, measuring a lump on the arm, and trying to determine whether that represents tuberculosis infection, or infection with other mycobacteria, or some non-specific response.

Cases are defined largely by the isolation of tubercle bacilli. Despite many improvements, the bacteriologic methods being used are basically the same as those developed by Pasteur, Ehrlich and Koch. Organisms are stained, viewed under the microscope, and cultured. The culture step is a procedure which still takes weeks to months to perform and then requires further biochemical and other tests to differentiate tubercle bacilli from other mycobacteria.

With the advent of genetic probe technology, which provides sequences of nucleic acids which are complementary to those of the organism sought to be detected, in this case, *Mycobacterium tuberculosis*, the authors of the "Pittsfield Report" at p. 76 recognized the importance of discovering a way to liberate nucleic acids within mycobacterial microorganisms so that they will be available for hybridization with the complementary probe:

"A key aspect in the clinical use of DNA probes for mycobacteria detection is sample handling. A basic requirement of the test is that the sample nucleic acids must be made available for hybridization to the probe. The hybridization technique is applicable to sputum, feces, serum, tissue homogenates, spinal fluid and urine."

Furthermore, in reference to clinical methodology, the report went on to state:

"A major difficulty in utilizing DNA probes to detect Mycobacteria is breaking the Mycobacterial cells to free nucleic acids for hybridization. There are no described ways to do this and development techniques to accomplish this are important." [Emphasis Added]

The need for a simple way to safely break cells in an efficient manner suitable for the clinical laboratory is clear. For a general overview of cell fractionation and disruption techniques, see Schnaitman, C. A., "Cell Fractionation," *Manual of Methods for General Bacteriology*, Ch. 5, 52–61 (Gerhardt, P. et al, Eds. 1981), Coakley W. T. et al., "Disruption of Microorganisms," *Adv. Microbiol. Physiol.* 16:279–341 (1977) and Hughes, D. E. et al, "The Disintegration of Micro-organisms," *Methods in Microbiology*, 5B, Ch. 1, 2–54 (Norris, J. R. and Ribbons, D. W., Eds. 1971).

Prior art methods for extracting RNA or DNA from refractory bacteria, such as mycobacteria, include resorting to rigorous physical grinding or shaking of the organisms to permit release of their cellular constituents. (See, H. Venner, *Acta Biol. Med. Ger.*, 11:806 (1963); M. Tsukamura, et al., *Am. Rev. Respirat. Diseases*, 81:403 (1960); Moore, et al., U.S. Pat. No. 4,295,613, entitled "Apparatus For Breaking Bacterial Cells", issued Oct. 20, 1981). Such methods present considerable drawbacks. Firstly, friction resulting from the physical interaction of the grinding particles can create excessive heat which has deleterious effects on the genetic cellular constituents such as DNA and RNA and can render them unusable in subsequent diagnostic procedures.

Also, many organisms, which heretofore required such harsh conditions for extraction of their cellular components, are extremely pathogenic. The health hazards associated with the grinding of these masses of pathogens in open systems are obvious.

Recognition of these problems has led some researchers to seek alternative approaches to refractory cell disruption. (See, for example, L. G. Wayne and G. A. Diaz, *J. Bacteriol.*, 93:1374 (1967); L. G. Wayne and W. M. Gross, "Isolation Of Deoxyribonucleic Acid From Mycobacteria," *J. Bacteriol.*, 95:1481, (1968), in which cultures of *Mycobacterium tuberculosis*, *M. kansasii*, *M. avium*, *M. gastri*, *M. flavescens*, *M. smegmatis*, *M. phlei* and Group II scotochromogenic mycobacteria grown in glycerol-rich medium under strongly aerobic conditions undergo autolysis after abrupt exposure to oxygen limitation.) This alternative procedure is time consuming, expensive and requires a large number of procedural steps including a step in which the organism must be grown.

Perhaps the most effective prior art method for breaking open mycobacterial cells is the use of a pressure cell. With this method the solution of mycobacterial microorganisms is passed through a very small diameter hole under very high pressure. During passage through this tiny hole, the mycobacteria are broken open by the mechanical forces and their internal contents are spilled into solution. The extent of cell rupture rate utilizing this method ranges from 90 to 100%. However, such a system is large, expensive and requires a cooling system to prevent excessive heat from building up and damaging the contents of the lysed cells. Large samples are required and the instrument needs to be cleaned and decontaminated between runs. Finally, a large containment system is required when infectious material is handled.

Alternatively, a solution containing mycobacterial microorganisms can be subjected to very intense ultrasonic bombardment which results in cell breakage. Some researchers have utilized ultrasonic devices such as powerful ultrasonic probes (known as sonifiers or sonicators) in order to break open cells. (See, Seiter, J. A. and Jay, J.M., "Application of Polyacrylamide Gel Electrophoresis to the Characterization and Identification of Arthrobacter Species," *Int. J. Syst. Bacteriol.*, 30:460–465 (April, 1980.)) However, this study involving the protein characterization and identification of certain Arthrobacter species utilized a model W350 sonicator (Heat Systems—Ultrasonics, Inc.) with beads to disrupt large volumes of cell suspensions. The suspensions in Seiter, et al. were then centrifuged to remove particulate matter and the supernatant was collected and subjected to polyacrylamide gel electrophoresis, and protein profiles were established. As significant amounts of heat are generated with high-powered probe devices of this type, cooling jackets or ice baths are required to reduce escalating temperatures which can and often do damage cellular RNA or DNA in a manner in which they are no longer detectable with probe technology. This fact has been demonstrated in a number of references. For example, in Salter, D. N. and Smith, R. H., "Protein Utilization in the Young Steer: Digestion and Nitrogen Retention of $^{15}$N-Labelled Rumen Bacterial Protein", *British Journal of Nutrition*, 51:531–539 (1984), a suspension of rumen bacteria was disrupted by ultrasonic treatment of ice-cooled portions of suspension with added glass beads using an ultrasonic disintegrator (Soniprobe; Dawe Instruments Ltd., London). This treatment caused a gradual rise in temperature to 25°–30° C. and disruption of approximately 95% of the total bacteria. However, analysis of the bacterial suspension before disruption and after the final dialysis of the disrupted bacterial debris showed that RNA and DNA were completely destroyed by this process.

Such probe-type sonicating devices can have measured outputs as high as 80–100 W. (See, Closs, O., et al., "The Antigens of *Mycobacterium boris*, Strain BCG, Studied by Crossed Immunoelectrophoresis: A Reference System", *Scand. J. Immunol.*, 12:249–263 (1980).

In this study, suspensions of *Mycobacterium bovis* bacilli were sonified in a rosette-cooling cell submerged in ice water using a Branson sonifier model B-12 (Branson Sonic Power Co., Danbury, Conn.) at a measured effect of 80–100 W in order to elucidate the antigenic composition of *Mycobacterium bovis*. (Also see Alliger, H., U.S. Pat. No. 3,558,066 entitled "Ultrasonic Extraction of Viable Antigens From Gram-Positive Bacteria," issued Jan. 26, 1971.) In contrast, the ultrasound baths utilized in the method according to the present invention operate at lower power densities and are convenient, inexpensive and compact. There is no need for cooling jackets or ice-baths since the units lack the power to raise the temperature of the sonicating suspension to damaging levels. In addition, this method can handle infectious material in a safe manner. The ultrasonic baths can be placed in a biological safety cabinet and the tubes can be closed ensuring that no hazardous aerosols are produced. Finally, many samples can be processed simultaneously.

In conclusion, the prior art pressure cells and powerful sonicator probe devices are time consuming, expensive and difficult to use in a safe and efficient manner.

Accordingly, it is a principal object of the present invention to provide a simple and inexpensive method for disrupting cells to facilitate release of the cellular constituents contained therein. Additionally, it is a further object of the present invention to provide a method for releasing RNA and DNA from microorganisms without causing significant damage to the nucleic acids contained therein. It is a further object of the present invention to provide a method for releasing RNA and DNA from microorganisms contained in an unpurified biological, environmental, food, or clinical sample. A still further object of the present invention is to provide a rapid, efficient and inexpensive method for the in-sample release of RNA and DNA from unpurified biological or clinical samples such as sputum, feces, serum, tissue, blood, urine, spinal or synovial fluid or any other bodily fluid thought to contain microorganisms to facilitate the detection, identification or quantification of said microorganisms from a sample in an open or closed container. A still further object of the present invention is to provide a method for the release of intracellular materials from refractory microorganisms.

SUMMARY OF THE INVENTION

Generally stated, the present invention accomplishes the above-described objectives by the surprising discovery that cells or microorganisms in a solution with small beads of various composition, for example, glass, plastic, sand or silicates, latex, crystals, metals, metal oxides, etc., in a container, when subjected to sonication in, for example, an ultrasound bath (such as, for example, the type used for cleaning jewelry or laboratory apparatus), released their cellular constituents including RNA and DNA into solution within minutes. The results indicated that the nucleic acids could readily be detected by nucleic acid hybridization techniques and were not destroyed as sometimes occurs with other types of ultrasound devices. Cell breakage occurred easily with all microorganisms tested including the usually refractory mycobacteria. The released RNA and DNA in solution within the container is then available for, for example, hybridization with complementary sequences of nucleic acids present in genetic probes. This method could also be utilized to release protein and cell components for antibody reactions. The container in which the solution of cells and beads are placed can be, for example, a plastic test tube or other suitable container with suitable closure. Alternatively, ultrasonic energy can be transmitted directly to the solution or suspension of cells and beads through, for example, a transducer thus obviating the need for a separate container to hold the cells and beads. A variety of additives such as buffers, detergents, genetic probes, antibodies, enzymes, chelators, salts, organic compounds, etc., can also be present in order to provide the proper conditions for reaction of the released RNA or DNA with the genetic probe after the ultrasound treatment according to the method of the invention has disrupted the cells. Therefore, one of the embodiments of the method of the present invention discloses a one-step, in-sample method for lysing or disrupting cells in an unpurified clinical or biological sample, thereby facilitating release of genetic material into solution for hybridization with genetic probes whose nucleic acid sequence is complementary to that of the RNA or DNA of the organism whose presence is to be detected. The other additives present in the solution can be varied by one skilled in the art to provide the reaction conditions best suited to the requirements of the particular procedure.

DETAILED DESCRIPTION OF THE INVENTION

In a broad aspect, the method of the present invention is based on the surprising discovery that cells in solution with small beads in a container, when exposed to sonication in, for example, an ultrasound bath, disrupt, causing release of their cellular components into the solution within a container which can be closed if necessary. Among those cellular components whose release is facilitated by the method of the present invention are deoxyribonucleic acid (DNA) and ribonucleic acid (RNA).

Certain types of cells have proven to be very difficult to break open. One such type of cell, *Mycobacterium tuberculosis*, is a rod shaped bacterium (bacillus) with a dense cell wall composed of complex lipids. These bacteria are notoriously difficult to break open. As a result, harsh conditions have been proposed and utilized to disrupt these cells, some of which have resulted in deleterious effects which render the nucleic acids damaged and unusable for subsequent procedures or experimentation. However, the need to lyse such types of cells in an expedient, safe, efficient and inexpensive manner is a continuing and urgent one.

The clinical use of DNA or RNA probes for mycobacterial detection has been hampered by the major difficulty encountered in breaking the mycobacterial cells to make the nucleic acids contained therein available for hybridization. Without this basic requirement, namely, efficient, safe and inexpensive release of cellular RNA and DNA into solution, hybridization cannot occur and the value of genetic probes as a diagnostic tool for refractory cells such as mycobacteria is reduced significantly. Prior to applicant's invention, no simple ways were described for adequately disrupting these cells without making the RNA and/or DNA incapable of hybridization.

There are a variety of ultrasonic baths commercially available which could be utilized to practice the method of the present invention. For example, Branson Cleaning Equipment Company of Shelton, Conn. markets about a dozen models under the Bransonic ® name with tank capacities ranging from 10 ounces to 8 gal- Ions. Mettler Electronics ® of Anaheim, Calif. also markets several models with tank capacities ranging from 2.1 quarts to 18 gallons. These ultrasonic baths are recommended for cleaning tools, pens, jewelry, machinery, engine parts, nozzles, laboratory equipment, switches, locks, automobile parts, glass, ceramics, metals, hard plastics, etc. Ultrasonic cleaning baths such as these utilize a piezoelectric transducer such as, for example, lead zirconate titanate or barium titanate or a magnetorestrictive transducer to convert electrical input energy into high frequency ultrasonic energy. This mechanical energy, or vibration, is then coupled into and transmitted through the liquid contained in the cleaning tank. Bransonic ® ultrasonic cleaners operate at frequencies around 55 KHZ, whereas the nominal main frequencies of the Mettler ® devices above range from 22–67 KHZ. The term ultrasonic refers to frequencies just above the range of human hearing, hence about 20 KHZ. Alternatively, ultrasonic energy can be delivered directly to the solution or suspension of cells and beads through, for example, a transducer, thus obviating the need for a separate container to hold the cells and beads. A solution or suspension of cells or microorganisms in purified or unpurified form can be placed in, for example, a vessel or well or a series of vessels or wells composed of a material, such as stainless steel, capable of transmitting ultrasonic energy. The well is either attached to or is in proximity to a suitable transducer or other device capable of translating input energy into ultrasonic energy. The cells and beads can be placed directly into the well or series of wells which act as sample holders, or, alternatively the cells and beads can be placed in containers and submerged in liquid contained within the well. The well can be capped off with a suitable closure to prevent leakage or aerosol formation. It should be understood that the above-described embodiments are illustrative only and can be embodied in other specific forms consistent with the spirit and essential attributes of the present invention.

While the method by which ultrasound disrupts cells has not been fully elucidated, it is postulated that ultrasonic waves traveling through a liquid consist of alternate compressions and rarefactions. If the amplitude of the wave is high enough, a phenomenon known as cavitation is produced. Cavitation is the making and breaking of microscopic bubbles. As these bubbles or cavities grow to what is known as resonant size, they collapse instantly and violently in one compression cycle, producing high local pressure changes or perhaps 20,000 atmospheres. This mechanical shock, which is felt at a distance of a few microns, is responsible for cellular disruption in the case of the high power density instruments. (Alliger, H. *Ultrasonic Disruption*, reprinted from *American Laboratory*, October 1975.)

In the method according to the present invention, however, the cells are not believed to be broken by cavitation. This is believed to be true because the cells are not broken in the absence of the small beads. Instead, the ultrasound is believed to cause the beads to vibrate through the bacterial suspension or solution resulting in breakage of the cells by shear. While the precise interaction between the minute beads and the ultrasonic waves is not known and applicants do not wish to be bound or limited by any theory, it is believed that the ultrasound waves impart pulsatile motion to the beads. The cells are then subjected to the high shearing activity of the moving beads which results in cell wall rupture and subsequent release of the cellular components. However, it is important to prevent damage to the cellular components once released into solution. The low power density of the ultrasound bath of the present invention while sufficient to disrupt cells is not powerful enough to destroy RNA or DNA once released. Furthermore, experiments have shown that the method of the present invention is effective in disrupting cells at room temperature (18° C.) and above. However, this parameter is not deemed to be a limitation to the effective temperature range of the present invention.

It has been found that the ultrasound method according to the present invention is effective in breaking open cells of even refractory microorganisms such as mycobacteria, in a rapid, safe, efficient and inexpensive manner facilitating the release of cellular components including RNA and DNA.

Applicants compared their method to the method for disrupting cells utilizing a pressure cell. The pressure cell method was selected as the reference method for this comparison since virtually all of the bacteria are broken open using this method. Mycobacteria were used as the bacteria in solution. The general protocol for the above comparison is described as follows:

A. A solution containing mycobacteria was split into four aliquots.
  1) One aliquot was passed through a pressure cell twice at 18,000 psi.
  2) A second aliquot was added to glass beads in a closed container which was placed in an ultrasound cleaning bath and subjected to ultrasound treatment according to the present invention.
  3) A third aliquot was placed in a closed container without glass beads and subjected to ultrasonic treatment as in (2).
  4) A fourth aliquot was untreated and served as a control.

B. Each aliquot of A. was then assayed to determine the fraction of cells which were disrupted. The amount of RNA released in each sample by the specific treatment was determined by nucleic acid hybridization kinetics. An aliquot of each sample was adjusted to 0.48 M phosphate buffer (PB), 0.2% sodium dodecyl sulfate (SDS). Radioactive DNA complementary to *Mycobacterium tuberculosis* RNA was added to each sample and the sample incubated at 72° C. At specified times aliquots were removed from each sample and diluted into 0.14 M PB, 0.02% SDS. The diluted sample was then assayed on a hydroxyapatite (HA) column equilibrated to 72° C., 0.14 M PB, 0.02% SDS. The basic HA fractionation procedure is described in Kohne and Britten, *Procedures in Nucleic Acid Research* (*1971*), eds. Cantoni and Davies, Harper & Row, Vol. 2, p. 500 (1971). The kinetic profile of the samples were then compared to determine the concentration of free RNA in each sample.

C. Results are reported in Table I.

TABLE I

| CELL TREATMENT METHOD | FRACTION OF CELLS DISRUPTED |
|---|---|
| 1. Pressure Cell Method - passed through pressure cell twice at 18,000 psi. | 100% |
| 2. 10 minutes in ultrasound cleaning bath with glass beads. | 100% |
| 3. 10 minutes in ultrasound cleaning bath without glass | 15% |

TABLE I-continued

| CELL TREATMENT METHOD | FRACTION OF CELLS DISRUPTED |
|---|---|
| beads. | |
| 4. Control. | 12% |

Comparisons of cracking in the ultrasonic cleaning bath and cracking using the French pressure cell were also made with a number of different types of bacteria. The samples were divided into two parts. 100 μl ml of one part was added to a tube containing an equal volume of glass beads and was treated in an ultrasonic bath for 10 minutes at 75° C. using degassed water (the degassing procedure consisted of filling the ultrasonic bath with boiled water and turning the ultrasonics on for 15 minutes when the temperature falls to 90° C.). The sample was then diluted 10 fold and centrifuged for 30 minutes at 3400 rpm in a Sorvall RC-3B centrifuge using an H6000A rotor to spin down the particulate matter. The second part of each sample was passed through a French pressure cell, then diluted 10 fold with water and centrifuged as above. Release of cell material was measured by examining the u.v. absorbance at 255 nm. The absorbance at 255 nm is taken as an index of cell cracking. Nucleic acids and proteins are the major substances contributing to the absorbance at this wavelength. The results are shown below in Table II in units of $A_{255}$ released into the supernatant from the same suspension.

TABLE II

| Organism | $A_{255}$ Sonication | $A_{255}$ French Pressure Cell |
|---|---|---|
| *Legionella pneumophila* | 0.961 | 0.170 |
| Baker's yeast | 1.229 | 1.299 |
| *Mycobacterium nonchromogenicum* | 0.201 | 0.018 |
| *Escherichia coli* | 1.607 | 0.973 |
| *Staphylococcus aureus* | 0.337 | 0.028 |
| *Bacillus subtilis* | 0.960 | 0.039 |

*Legionella pneumophila* and *Escherichia coli* are examples of Gram-negative rods. *Bacillus subtilis* is a Gram-positive rod. *Staphylococcus aureus* is a Gram-positive coccus, while *Mycobacterium nonchromogenicum* is an acid-fast bacterium. Finally, Baker's yeast is a representative of a nonbacterial group of organisms. All of these organisms, having diverse types of cell walls, were easily broken using the present invention.

According to the disclosed method it has been found that disruption of cells, even refractory cells, occurs even with the very low power densities as long as beads are also present in solution. When ultrasonic probes are placed directly into containers of cell suspensions at ultrasonic power densities of 0.2-3.0 W/ml, it is likely that surface activity and shock waves are mainly responsible for cell disintegration. (See Coakley et al, supra at p. 303) However, applicants have compared the relative power densities of the present invention with a typical high power density probe sonic oscillator and have found that the method of the present invention is successful at disrupting cells at a power density significantly lower than 0.2 W/ml as long as beads are also present in solution. A high power density probe sonic oscillator was operated in 200 ml of water for 5 min. A temperature change of 8.95° C. was effected. This translated to a power of 8.95×200 or 1790 cal/5 min, or a power of 25 W. In a typical experiment most of this power is concentrated within 3 ml of the probe tip, resulting in a power density of about 8.3 W/ml. In comparison, the temperature rise resulting from operating a typical ultrasound bath containing 250 ml of water for 10 min. is 10.4° C. This translates to a power of 18 W per bath. In a typical cell cracking experiment according to the present invention, the bath contains 750 ml of water. This gives a power density of 0.024 W/ml. According to this comparison, the probe sonic oscillator has a power density over 300 times as great as the water bath cleaner. However, applicants have found that when the cell solution also includes particulate beads as disclosed above, cell disruption occurs even at these low power densities.

In other experiments suspensions of mycobacteria in 1% sodium dodecyl sulface (SDS) were prepared and counted using a Petroff-Hausser counting chamber. They were adjusted to $7 \times 10^8$/ml by diluting with 1% SDS and cracked using a French pressure cell at 1000 psi. A 1 ml sample of the same suspension was added to a capped Eppendorf tube containing 0.1 ml of glass beads (0.1-0.3 mm) and sonicated in a water bath cleaner (Mettler Electronics Cavitator ME 4.6) for 10 minutes at room temperature. The degree of cracking was determined by measuring the amount of RNA released using a probe assay.

Reagents

Reagent 1
0.96 M Sodium Phosphate buffer, pH 6.8
2.0% SDS
1 mM EDTA
1 mM EGTA
Probe Solution
3.5 ml Reagent 1
30 microliters of $^{125}$I labeled TB probe in 0.14 M Phosphate buffer and 0.02% SDS, with an activity of 8,000 cpm/microliter
Reagent 2
0.14 M Sodium Phosphate buffer, pH 6.8
0.02% SDS
1 g Hydroxyapatite (HA)/50 ml
Reagent 3
0.14 M Sodium Phosphate buffer, pH 6.8
0.02% SDS Procedure: Samples consisted of 100 μl of cracked cell suspension and 100 μl of probe solution. The positive control consisted of 100 μl of probe solution and 10 μl of (0.5 μg/10 μl TB RNA) and 90 μl of water. The negative control contained 100 μl of probe solution and 100 μl of water. Total counts were determined with 100 μl of probe.

Individual sample tubes were prepared for each time point. Samples of each cracked organism suspension were assayed at 15, 30 and 120 minutes. Samples and control were incubated at 72° C. After incubation 5 ml of reagent 2 were added to all samples and controls except total counts and the HA control, and the samples were vortexed. After incubation for 5 minutes at 72° C. the tubes were vortexed and spun for 1 minute at 1500 rpm in the IEC 36 well centrifuge. The supernatant was decanted, and 5 ml of reagent 3 were added to all samples and controls except the total counts sample. The samples were vortexed and spun as before. The supernatant was decanted and 5.5 ml cytoscint was added, vortexed and the tube counted in a scintillation counter.

The counts of the HA samples were considered background and subtracted from each sample and the total counts. The resulting counts per sample were divided by the resulting total counts and multiplied by 100 to obtain a % hybridization (% hyb).

The highest value of the % hyb in a given set was the % max. The % single stranded (% SS) is equal to 100(% max-% hyb)/% max. The log (% SS) was plotted against time and the $t_{\frac{1}{2}}$ determined from the time at which the % SS=0.5. The RNA concentration is:

$$[RNA] = 2(0.0023)/0.011/t_{\frac{1}{2}}$$

The 0.0023 is the value for the half Cot for the TB probe. The value 0.011 is the factor for converting optical density to micromoles and the factor 2 is required to bring the concentration to that of the original cracked solution.

The number of cell equivalents of RNA was determined to be $5.5 \times 10^{-9}$ μg/cell.

Results: The ratio of RNA released from a given suspension of cells using the ultrasonic cleaning bath with glass beads (Son.) to the French Pressure Cell (F.P.) is shown below in Table III.

TABLE III

| Bacterium | $t_{\frac{1}{2}}$ (hrs) F.P. | $t_{\frac{1}{2}}$ (hrs) Son. | Ratio of RNA released by Son./F.P. |
|---|---|---|---|
| M. flavescens | 0.08 | 0.18 | 0.44 |
| M. gordonae | 0.25 | 0.44 | 0.56 |
| M. phlei | 0.075 | 0.15 | 0.48 |
| M. simiae | 0.58 | 0.64 | 0.90 |
| M. fortuitum | 0.14 | 0.31 | 0.47 |
| M. terrae | 0.095 | 0.098 | 0.98 |
| M. nonchromogenicum | 0.325 | 0.35 | 0.92 |
| M. malmoense | 0.55 | 0.67 | 0.82 |
| M. asiaticum | 0.42 | 0.30 | 1.39 |
| M. vaccae | 0.17 | 0.055 | 3.17 |
| M. smegmatis | 0.10 | 0.17 | 0.57 |
| M. gastri | 0.18 | 0.29 | 0.58 |
| M. szulgai | 0.89 | 0.41 | 2.13 |
| M. triviale | 0.22 | 0.20 | 1.11 |
| M. haemophilum | 0.15 | 0.18 | 0.85 |
| M. kansasii | 0.25 | 0.67 | 0.36 |
| M. marinum | 0.13 | 0.17 | 0.78 |
| M. bovis | 0.10 | 0.21 | 0.49 |
| M. bovis (BCG) | 0.11 | 0.17 | 0.68 |
| M. africanum | 0.065 | 0.22 | 0.30 |
| M. thermoresistibile | 0.28 | 0.54 | 0.51 |
| M. tuberculosis | 0.19 | 0.41 | 0.45 |
| M. chelonae | 0.29 | 0.18 | 1.60 |
| M. scrofulaceum | 0.81 | 0.52 | 1.57 |
| M. avium | 0.16 | 0.25 | 0.65 |
| M. intracellulare | 0.35 | 0.37 | 0.92 |

This example illustrates that these twenty-six strains of mycobacteria were all disrupted using the ultrasonic cracking method described above.

The method of the present invention has been utilized to disrupt cells in a large variety of other organisms, less refractory than *M. tuberculosis*. Cell disruption was verified by standard hybridization assays with genetic probes. The resulting strong hybridization values indicated complete cell cracking and intact RNA availability.

Experiments were conducted in an effort to determine optimal conditions for cell disruption. Eight sets of experiments were run to determine the relative importance of three variables on the extent of cell disruption. Those three variables included:

(1) The amount of gas present in the bath water,
(2) The temperature of the bath water, and
(3) The quantity of beads present in the tubes.

A two-level factorial design was run using the following coding (See, DuPont—"Strategy of Experimentation", Rev. Ed. p. 20ff, Wilmington, Del., October 1975):

| Degas | Temperature | Bead Quanity |
|---|---|---|
| + = degassed | + = 70° C. | + = 0.5 ml |
| − = not degassed | − = 30° C. | − = 0.1 ml |

The coding for any of the following experiments is designated by a series of three signs, the first is the degassing condition, the second is the bath temperature and the third is the quantity of beads.

The assay protocol was as follows. A 1 ml cell suspension of *Mycobacterium nonchromogenicum* containing $7 \times 10^8$ cells/ml is added to an Eppendorf tube containing a measured quantity of glass beads. The tube is then placed in an ultrasound water bath for 10 minutes according to the method of the present invention. A control was prepared and treated in the same manner but was not sonicated. The samples and controls were centrifuged to pellet the unbroken cells and the release of cell material was measured by examining the U.V. absorbance at 255 nm ($A_{255}$ hybridization) as described above.

The degassing procedure consisted of filling the ultrasonic bath with boiled water and turning the ultrasonics on for 15 minutes when the temperature falls to 90° C. Experimental results are shown below in Table IV.

TABLE IV

| Experiment | Code | Average Value | Experiment | Code | Average Value |
|---|---|---|---|---|---|
| 1A | − − − | 0.035 | 1B | − − + | 0.88 |
| 2A | + + − | 0.201 | 2B | + + + | 0.219 |
| 3A | + − − | 0.087 | 3B | + − + | 0.150 |
| 4A | − + − | 0.107 | 4B | − + + | 0.168 |

The computed factor effects are:

| | |
|---|---|
| (1) Degassing | 0.065 |
| (2) Temperature | 0.082 |
| (3) Bead quantity | 0.049 |

The minimum significant factor was computed to be 0.024. Thus, all factors treated are significant in cell rupture. Cellular disruption is favored by maintaining the water bath at higher temperature, using a degassed water bath and by increasing the quantity of beads present in the tubes.

It is understood that the beads utilized in the present invention can be composed of a variety of different materials of different shapes and sizes, while many of the commercially available types of beads are generally spherical or globular in shape, many beads may have irregular shapes and still be effective. Commercially available beads include, for example, Amberlite, Dowex, Impandex, Potters, etc. However, other types of glass beads, plastics, crystals, metals, metal oxides, latex and granular or particulate materials such as sand or silicates can also be used in the present invention. Therefore, it should be understood that beads or equivalent granular or particulate material can be used without departing from the spirit or essential attributes of the method according to the present invention.

Suspensions of *Mycobacterium nonchromogenicum* were sonicated according to the disclosed methodology using beads composed of differing types of materials.

After sonication, the $A_{255}$ assay protocol described above was employed to determine cell breakage rates with different bead types. The results are disclosed in Table V below.

TABLE V

| Bead Type | $A_{255}$ Assay |
|---|---|
| Glass | 0.423 |
| Amberlite | 0.101 |
| Dowex 50 | 0.287 |
| Sand | 0.180 |

Furthermore, beads of different sizes and types of glass were subjected to sonication with *Mycobacterium nonchromogenicum* under the aforementioned conditions to determine the effect of bead size and composition on rupture rate. The results were normalized to the fraction of breaking using Impandex beads as the standard. The previously described $A_{255}$ assay was used to measure the results which are disclosed below in Table VI.

TABLE VI

| Designation | Size in mm | $A_{255}$ | $A_{255}/A_{255}$ Impandex |
|---|---|---|---|
| PO337 | 0.850–0.600 | 0.402 | 0.73 |
| HO0337 | 0.850–0.590 | 0.090 | 0.16 |
| PO060 | 0.150–0.106 | 0.517 | 0.95 |
| HO05 | 0.106–0.075 | 0.0 | 0.0 |
| Impandex | 0.3–0.2 | 0.546 | 1.0 |
| PO120 | 0.300–0.212 | 0.379 | 1.13 |
| Impandex | 0.3–0.2 | 0.335 | 1.0 |
| HO120 | 0.300–0.212 | 0.282 | 0.65 |
| Impandex | 0.3–0.2 | 0.432 | 1.0 |

H = Potter's Barium Titanate Glass (High density)
P = Potter's Soda-Lime Glass (Low density)

As can be seen from the data in Table VI, beads of various types of glass can be advantageously used in the method of the present invention. Also, the size of the beads appears to have an effect on the degree of cell disruption. Experiments indicate that beads with diameters ranging from about 0.05 mm to about 1.0 mm are effective in disrupting cells. However, the method of the present invention is applicable to a wide variety of sizes and types of beads and this range is not deemed a limitation. Furthermore, the high density Barium Titanate glass designated with the prefix H above does not appear to work as well as the other lower density glasses.

Once the cells have disrupted and the contents have spilled out into solution, the genetic materials are available for hybridization with genetic probes. The genetic probes are composed of nucleic acids whose sequence is complementary to that of the organism whose presence is to be identified, detected or quantified. The hybridization reaction procedure is disclosed in two pending patent applications, "METHOD FOR DETECTION, IDENTIFICATION AND QUANTITATION OF NON-VIRAL ORGANISMS", Ser. No. 456,729 and "METHOD FOR DETECTING, IDENTIFYING AND QUANTITATING ORGANISMS AND VIRUSES", Ser. No. 655,365, filed Jan. 10, 1983 and Sep. 4, 1984, respectively. These disclosures are incorporated herein by reference.

In order to facilitate hybridization of the genetic material released from the cells, with the complementary sequences of nucleic acids in the genetic probes, the container which holds the cells and beads may also contain a variety of additives designed to provide optimal reaction conditions for accelerated hybridization. Such additives may include buffers, chelators, organic compounds and nucleic acid precipitating agents such as detergents, dihydroxybenzene, sodium dodecyl sulfate, sodium diisobutyl sulfosuccinate, sodium tetradecyl sulfate, sarkosyl and the alkali metal salts and ammonium salts of $SO^{-2}_4$, $PO^{-3}_4$, $Cl^{-1}$ and $HCOO^{-1}$. Such additives can be utilized by one skilled in the art to provide optimal conditions for the hybridization reaction to take place. These conditions for accelerated hybridization of single stranded nucleic acid molecules into double stranded molecules are the subject of two pending U.S. patent application, "ACCELERATED NUCLEIC ACID REASSOCIATION METHOD", Ser. No. 627,795, filed Jul. 5, 1984 and "ACCELERATED NUCLEIC ACID REASSOCIATION METHOD", filed Jan. 6, 1986 which is a continuation-in-part application of above.

The method of the present invention can be carried out on cells or microorganisms from purified samples or unpurified clinical or samples such as sputum, feces, tissue, blood, spinal or synovial fluids serum, urine or other bodily fluids, or other samples such as environmental or food samples. Prior to delivery of the ultrasonic energy to the cells or microorganisms according to the method of the present invention, the cells or microorganisms can be suspended or placed in solution. Cells may also be centrifuged or made into a paste prior to treatment. In the case of the unpurified samples referred to above, the cells or microorganisms may remain intact and untreated in their own biological environment prior to delivery of ultrasound energy. These samples may be obtained directly from a patient suspected of carrying a pathogenic microorganism and immediately collected in a suitable container which contains beads. Environmental samples such as water samples or samples of food thought to be contaminated with microorganisms can also be applied to the present invention. The container may then be capped and subjected to ultrasound energy according to the present invention. For purposes of clarity, the terms solution and suspension shall be used interchangeably.

As a result of applicants' discovery, cells or microorganisms present in an unpurified biological or clinical sample in solution in a closed or open container with small beads, when subjected to ultrasound treatment in, for example, a low powered ultrasound bath, lyse or disrupt and as a result make available RNA and DNA into the solution. The RNA and DNA retains its ability to bind complementary probe, thus it is not significantly damaged according to the method of the present invention since such a low power density is generated. The nucleic acid of the microorganism is then available for accelerated hybridization with genetic probes while still present in the same container. Therefore, a rapid and efficient system is disclosed for a closed, in-sample, one-step method for disrupting cells in a clinical, environmental, food or biological sample, facilitating release of RNA and DNA, and then hybridizing said nucleic acids with the genetic probe in solution. By such a method, microorganisms, such as, for example, mycobacteria, can be rapidly detected, identified and quantified from unpurified clinical samples of sputum, feces, tissue, blood, synovial or spinal fluids, serum, urine and other biological samples. The simplicity, ease, convenience and speed of such a system provide significant advantages over the complicated, multistep diagnostic procedures currently existing. Furthermore, this method should also be useful in liberating antigens from cells for reactions with proper antibodies.

It should be understood that the embodiments of the present invention disclosed herein are illustrative of the principles of the invention and that other modifications may be employed which are within the scope of the invention. Accordingly, the present invention is limited only in accordance with the scope of the appended claims.

What is claimed is:

1. A method for disrupting cells containing nucleic acid, said nucleic acid beige to bind to a complementary nuleic acid molecule, comprising the steps of:
   providing a sonic bath comprising a liquid,
   placing into said liquid a container comprising said cells in a second liquid, wherein said liquid in said bath does not enter said container,
   providing beads in said second liquid in contact with said cells in said container, wherein said beads have a diameter in the range of 0.05 to 1.0 millimeters, and
   subjecting said cells to ultrasonic energy from said sonic bath consisting essentially of sufficient power and duration to cause disruption of said cells and release said nucleic acid without destruction of the ability of said nucleic acid to bind to a complementary nucleic acid molecule compared to an intact nucleic acid molecule; wherein said energy is less than about 0.2 W/ml.

2. The method according to claim 1 wherein the frequency of said ultrasonic energy is greater than about 20 KHZ.

3. The method according to claim 1 wherein said beads are composed of a material selected from the group consisting of glass, plastic, latex, crystals, metals, metal oxides and non-glass silicates.

4. The method according to claim 1 wherein said cells are microorganisms.

5. The method according to claim 4 wherein said microorganisms are refractory.

6. The method according to claim 5 wherein said microorganism is a member of the genus Mycobacterium.

7. A method for releasing RNA and DNA from cells comprising placing a solution or suspension of cells from which RNA and DNA are to be released in a container which includes a quantity of beads having a diameter in the range of 0.05 to 1.0 millimeters and subjecting said container to ultrasonic energy of less than about 0.2 W/ml for an amount of time sufficient to cause said beads to disrupt said cells and release RNA and DNA therefrom into solution without destruction of the ability of said RNA and DNA to bind to a complementary nucleic acid molecule.

8. The method according to claim 7 wherein said ultrasonic energy is delivered to said cells from an ultrasound cleaning bath comprising a liquid.

9. The method according to claim 7 wherein said beads are composed of a material selected from the group consisting of glass, plastic, latex, crystals, metals, metal oxides, and non-glass silicates.

10. The method according to claim 8 wherein said liquid present in said ultrasound cleaning bath has a temperature greater than 18° C.

11. The method according to claim 8 wherein-the liquid present in said ultrasound cleaning bath is degassed prior to delivery of ultrasonic energy to said cells.

12. A method for releasing RNA and DNA from a microorganism from a clinical sample comprising placing said microorganism in a container in the presence of beads having a diameter in the range of 0.05 to 1.0 millimeters, placing said container in an ultrasonic bath, and subjecting said container in said ultrasonic bath to ultrasonic energy of less than about 0.2 W/ml for a time sufficient to disrupt said microorganism and release RNA and DNA therefrom into solution without destruction of the ability of said RNA and DNA to bind to a complementary nucleic acid molecule.

13. The method according to claim 12 wherein said clinical sample is obtained from sputum, feces, serum, blood, tissue, urine, spinal or synovial fluids.

14. A method for detecting the presence of a microorganism in a test sample comprising obtaining said sample suspected of carrying a microorganism whose presence is to be detected, placing said sample in a suitable container which includes beads having a diameter in the range of 0.05 to 1.0 millimeters, placing said container in an ultrasonic bath, subjecting said container in said ultrasonic bath to ultrasound energy of less than about 0.2 W/ml for an amount of time sufficient to disrupt said microorganism and release said microorganism's RNA and DNA into solution without destruction of the ability of said RNA and DNA to bind to a complementary nucleic acid molecule, hybridizing said RNA and DNA to nucleic acid probes containing nucleic acid sequences complementary to nucleic acid sequences of said microorganism, and detecting hybridization of said probes to said nucleic acid of said microorganism, wherein said hybridization is indicative of the presence of said microorganism.

15. The method according to claim 14 wherein said sample is obtained from a patient's tissue or fluid.

16. The method according to claim 14 wherein said sample is obtained from an environmental sample suspected of microbial contamination.

17. The method according to claim 14 wherein said sample is obtained from a food sample suspected of microbial contamination.

18. The method according to claim 14 wherein said container also includes additives to facilitate hybridization of said microorganism's released RNA or DNA with said genetic probe.

19. The method according to claim 18 wherein said additives comprise a buffer.

20. The method according to claim 19 wherein said buffer comprises sodium phosphate.

21. The method according to claim 18 wherein said additives comprise a chelator.

22. The method according to claim 21 wherein said chelator is selected from the group consisting of EDTA and EGTA.

23. The method according to claim 14 wherein said sample is obtained from a patient's sputum, blood, serum, urine, feces, spinal fluids or synovial fluids.

24. The method according to claim 18 wherein said additives comprise a nucleic acid precipitating agent.

25. The method according to claim 24 wherein said nucleic acid precipitating agent comprises a detergent selected from the group consisting of sodium dodecyl sulfate, sodium diisobutyl sulfosuccinate, sodium tetradecyl sulfate and sarkosyl.

26. The method according to claim 24 wherein said nucleic acid precipitating agent is selected from the group consisting of dihydroxybenzene, and the alkali metal salts and ammonium salts of $SO_4^{-2}$, $PO_4^{-3}$, $Cl^{-1}$ and $HCOO^{-1}$.

27. The method according to claim 1 wherein said beads comprise sand.

28. The method according to claim 7 wherein said beads comprise sand.

* * * * *